United States Patent [19]

Chicart et al.

[11] Patent Number: 5,281,645
[45] Date of Patent: Jan. 25, 1994

[54] BENZOPHENONES CONTAINING AN ESTER FUNCTIONAL GROUP AND THEIR USE IN POLYMERS

[75] Inventors: Philippe Chicart, Sainte-Marine; Michel Gay, Villeurbanne, both of France

[73] Assignee: Rhone-Poulenc Chimie, Courbevoie, France

[21] Appl. No.: 917,893

[22] Filed: Jul. 24, 1992

[30] Foreign Application Priority Data

Jul. 25, 1991 [FR] France .................. 91-9694

[51] Int. Cl.$^5$ .................. C08K 5/13; C07C 89/90; C07C 69/773; C07C 69/75; C07C 69/353
[52] U.S. Cl. .................. 524/291; 524/296; 524/299; 524/336; 524/337; 560/84; 560/85; 560/127; 560/193; 560/221
[58] Field of Search .............. 524/291, 296, 299, 336, 524/337; 560/84, 85, 127, 193, 221

[56] References Cited

U.S. PATENT DOCUMENTS

| | | | |
|---|---|---|---|
| 3,580,927 | 5/1971 | Wear | 524/335 |
| 3,644,485 | 2/1972 | Lappin et al. | 560/127 |
| 4,261,912 | 4/1981 | Tracy | 560/85 |
| 4,824,892 | 4/1989 | Eiglmeier et al | 524/291 |

FOREIGN PATENT DOCUMENTS

| | | |
|---|---|---|
| 3438190 | 4/1986 | Fed. Rep. of Germany . |
| 91/04243 | 4/1991 | PCT Int'l Appl. . |

*Primary Examiner*—Veronica P. Hoke
*Attorney, Agent, or Firm*—Finnegan, Henderson, Farabow, Garrett & Dunner

[57] ABSTRACT

The present invention relates to new hydroxybenzophenones containing an ester functional group and to the use of these compounds as UV absorbers in organic polymers. More precisely, the new hydroxybenzophenones are 1,3-di(4-benzoyl-3-hydroxyphenoxy)-2-propanol carboxylates which preferably have a molecular mass of at least 500.

These benzophenones can be employed as anti-UV agents in organic polymers, either by themselves or jointly with known benzophenones of lower molecular mass, such as 2-hydroxy-4-alkoxybenzophenones.

18 Claims, No Drawings

BENZOPHENONES CONTAINING AN ESTER FUNCTIONAL GROUP AND THEIR USE IN POLYMERS

The present invention relates to new hydroxybenzophenone compounds containing an ester functional group and to the use of these compounds as ultraviolet (UV) light absorbers in organic polymers and to organic polymers containing these compounds as UV absorbers.

2-Hydroxybenzophenones are known UV absorbers which are very widely employed for stabilizing polymers against the detrimental, degradative effects of light. They are efficient compounds for this purpose. However, because of their excessive volatility, they are sometimes lost too rapidly during the processing or in certain uses of polymers. Accordingly, the long-term protection of polymers that are to be exposed to light presents some problems when these materials are used.

In Patent JP-A-89/96,259, it has been proposed to graft 2-hydroxybenzophenone units onto polysiloxane chains. However, the synthesis of these compounds is relatively complicated and the desired degree of grafting of 2-hydroxybenzophenone units is not always easy to achieve accurately.

The present invention relates to simple compounds containing at least two 2-hydroxybenzophenone units and having a molecular weight of at least about 500.

These compounds are, more precisely, benzophenones of the general formula (I)

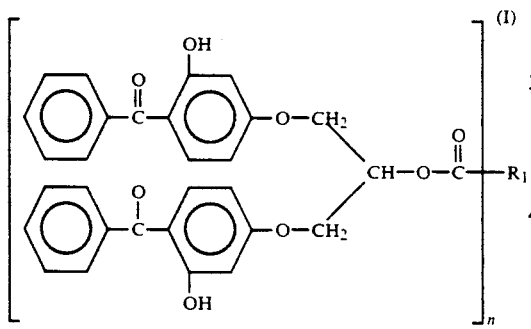

in which:

n represents 1 or 2;

$R_1$, when n is 1, is a radical having 6 to 40, preferably 12 to 40, and most preferably 14 to 30 carbon atoms and represents:
- a linear or branched alkyl radical,
- a phenyl radical,
- a phenyl radical containing 1 or 2 linear or branched alkyl substituents having from 1 to 6 carbon atoms, and/or a hydroxyl radical, $R_1$, when n is 2, is a radical having 6 to 40, preferably 12 to 40, and most preferably 14 to 30 carbon atoms and represents a linear or branched alkylene radical,
- an ortho-phenylene, meta-phenylene or para-phenylene radical,
- an ortho-phenylene, meta-phenylene or para-phenylene radical containing 1 or 2 linear or branched alkyl substituents having from 1 to 6 carbon atoms,
- an ortho-dialkylene cyclohexane radical in which the alkylene radicals, which can be linear or branched, identical or different, have from 1 to about 12 carbon atoms,
- a cyclohexylene or ortho-dialkylene cyclohexane radical cyclohexylene radical,
- a cyclohexylene or ortho-dialkylene cyclohexane radical as defined above, having 1 or 2 linear or branched alkyl substituents having from 1 to 6 carbon atoms.

The new benzophenone compounds containing an ester functional group according to this invention are more particularly compounds of general formula (I) in which:

n represents 1 or 2, $R_1$ represents, when n is 1, a linear of branched alkyl radical having 6 to 40 carbon atoms, such as, for example, hexyls, heptyls, octyls, nonyls, decyls, undecyls, dodecyls, tridecyls, tetradecyls, pentadecyls, heptadecyls or nonadecyls, $R_1$ represents, when n is 2:
- a linear or branched alkylene radical having 6 to 40 carbon atoms, such as, for example, hexamethylene, heptamethylene, octamethylene, nonamethylene, decamethylene, dodecamethylene, tetradecamethylene, hexadecamethylene, octadecamethylene, a cyclohexane-ortho-dioctamethylene radical containing 2 linear or branched alkyl substituents having 6 carbon atoms.

By way of nonlimiting examples of benzophenone compounds containing an ester functional group of formula (I) there may be mentioned:

1,3-di(4-benzoyl-3-hydroxyphenoxy)-2-propyl decanoate, 1,3-di(4-benzoyl-3-hydroxyphenoxy)-2-propyl dodecanoate (laurate), 1,3-di(4-benzoyl-3-hydroxyphenoxy)-2-propyl hexadecanoate, 1,3-di(4-benzoyl-3-hydroxyphenoxy)-2-propyl octadecanoate (stearate), 1,3-di(4-benzoyl-3-hydroxyphenoxy)-2-propyl docosanoate (behenate), bis[1,3-di(4-benzoyl-3-hydroxyphenoxy)-2-propyl] (4,5-dihexylcyclohexane)-1,2-di(octamethylenacarboxylate).

The benzophenone compounds containing an ester functional group of formula (I) can be prepared by reacting in the presence of an acid catalyst, 1,3-di(4-benzoyl-3-hydroxyphenoxy)-2-propanol formula (II):

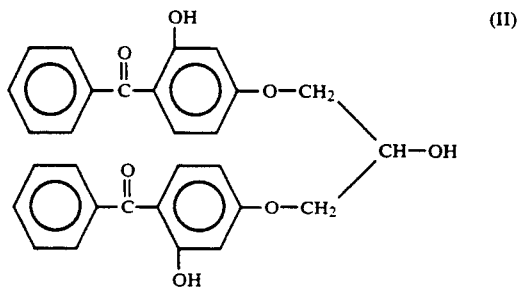

with an acid of general formula (III):

in which:

n represents 1 or 2; and

R₁ has meanings shown above in the case of the compounds of general formula (I).

1,3-Di(4-benzoyl-3-hydroxyphenoxy)-2-propanol of formula (II) is a known compound, preparation of which is described, for example, in Patent SU-A-277,764.

The acid catalyst employed for the esterification reaction of the alcohol of formula (II) with the acid $R_1\text{-}(COOH)_n$ can be any conventional acid catalyst for this type of reaction. The acid most frequently employed is para-toluenesulfonic acid.

The reaction is generally performed in a solvent, which makes it possible to remove the resulting water by azeotropic distillation. Thus, for example, toluene, benzene or xylene can be employed.

The reaction is carried out at a temperature of about 50° C. to 160° C. and preferably about 60° C. to 130° C. In practice, it is convenient to operate at the reflux temperature of the solvent employed. The reaction usually requires a number of hours, depending on the temperature selected and the specific acid catalyst employed.

The benzophenone compounds of formula (I) can be employed to advantage as UV absorbers in organic polymers that are subject to UV degradation. Thus, they can be employed as Uv absorbers in e.g., polyolefins such as polyethylene or polypropylene, polystyrenes, polyalkadienes, norbornene polymers, polyurethanes, polyethersulfones, polyetherketones, acrylic polymers, halogenated polymers and copolymers and mixtures thereof.

This invention also contemplates, therefore, organic polymer compositions stabilized with an effective quantity of at least one benzophenone of formula (I). For this purpose, it is preferred to employ benzophenones of formula (I) which have a molecular weight equal to or greater than about 600.

An advantageous alternative form of the invention consists in the use of at least one benzophenone compound of formula (I) in combination with a known benzophenone of lower molecular weight.

This alternative form of the present invention therefore relates to organic polymer compositions stabilized with an effective quantity of at least one benzophenone compound of general formula (I) and of at least one benzophenone of general formula (IV):

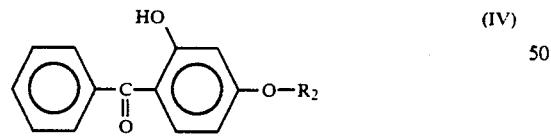

in which $R_2$ denotes a linear or branched alkyl radical having from 1 to about 30 carbon atoms.

The compositions of the invention usually contain:
either about 0.005% to 5%, preferably about 0.01% to 2%, by weight of benzophenone compound of formula (I) based on the weight of the polymer to be stabilized.
or about 0.005% to 5%, preferably about 0.01% to 2%, by weight of a mixture of benzophenone compound of formula (I) and of benzophenone of formula (IV) based on the weight of the polymer to be stabilized.

It is to be understood that the stabilized organic polymer compositions may contain a single compound of general formula (I) or a mixture of two or more compounds of formula (I).

The compounds of formula (I) or a mixture of compounds of formula (I) and of compounds of formula (IV) may be added to the polymer during or after the preparation thereof.

Organic polymer compositions containing the benzophenone compounds of formula (I) or mixtures of benzophenes of formula (I) and benzophenones of formula (IV) may additionally contain other additives and stabilizers which are usually employed in polymer formulations, such as, e.g.:

antioxidants, in particular the esters of 3-(3,5-di-t-butyl-4-hydroxyphenyl)propionic acid and more particularly tetrakis[3-(3,5-di-tert-butyl-4-hydroxyphenyl)propionyloxymethyl]methane and stearyl 3-(3,5-di-t-butyl-4-hydroxyphenyl)propionate, hindered amine light stabilizers (HALS) derived from 2,2,6,6-tetramethylpiperidine and more particularly bis(2,2,6,6-tetramethyl-4-piperidyl) sebacate, phosphites and phosphonites and more particularly tris(2,4-di-tert-butylphenyl) phosphite, metal deactivators, peroxide-destroying compounds, in particular thioethers, nucleating agents, fillers and reinforcing agents, plasticizers, lubricants, emulsifiers, pigments, optical whiteners, flame retardants, antistatic agents, blowing agents.

The stabilized polymer compositions can be used in a wide variety of forms, for example in the form of molded articles, sheets, fibers, cellular (bulk) materials, profiles or coating products, or as film-formers (binders) for paints, varnishes, adhesives or cements.

The examples which follow illustrate the invention, but are not intended to be limiting.

Preparation of the Product (Ia): Stearic Ester of 1,3-di(4-benzoyl-3-hydroxyphenoxy)-2-propanol This product is the compound of general formula (I) in which $R_1 = -(CH_2)_{16} - CH_3$.

The following were charged into a 500-cm³ three-necked round bottom flask fitted with a central stirrer, a thermometer and a Dean-Stark trap, supporting a condenser under nitrogen atmosphere:

45.0 g (0.093 mol) of alcohol of formula (II), 24.0 g (0.084 mol) of stearic acid, 1.0 g of para-toluenesulfonic acid, 350 cc of toluene.

The reaction mixture was heated to the reflux temperature of toluene for 24 hours. After returning to room temperature, the reaction mixture was washed three times with 150 cc of water. The nonhomogeneous organic phase was filtered and the solid recovered was a mixture of unreacted starting alcohol and acid. The organic phase was then dried over sodium sulfate and toluene was evaporated off at reduced pressure. The 50.5 g of crude product that was recovered was chromatographed on a silica gel column with 2/1 hexane/ethyl acetate elution to remove the alcohol and acid residues remaining in the product.

29.5 g of a pale yellow solid were finally obtained (this is a pure isolated product yield of 47% based on the starting acid).

The structure was confirmed by mass spectrometry and by proton magnetic resonance ($^1$H NMR). Purity was greater than 95%.

Physical characteristics

---
Melting point: 82° C.
UV (CHCl$_3$ solvent): ε 327 nm = 19290 l mol$^{-1}$ cm$^{-1}$
ε 287 nm = 30790 l mol$^{-1}$ cm$^{-1}$
---

EXAMPLE 2

Preparation of the product (Ib): Behenic acid ester of 1,3-di(4-benzoyl-3-hydroxyphenoxy-2-propanol This product is the compound of general formula (I) in which $R_1 = (CH_2)_{20} - CH_3$.

The following were charged into a 500 cc three-necked round bottom flask fitted with a central stirrer, a thermometer and a Dean-Stark trap, supporting a condenser under nitrogen atmosphere:

26.6 g (0.055 mol) of alcohol of formula (II), 17.0 g (0.050 mol) of technical behenic acid (predominantly docosanoic acid)

1.0 g of para-toluenesulfonic acid, 250 cc of toluene.

The reaction mixture was heated to the reflux temperature of toluene for 24 hours. After returning to room temperature, the reaction mixture was washed three times with 150 cc of water. The nonhomogeneous organic phase was filtered (the recovered solid was a mixture of unreacted starting alcohol and acid). The organic phase was then dried over sodium sulfate and the toluene was evaporated off at reduced pressure. The 31.0 g of crude product that was recovered was chromatographed on a column of silica gel with 2/1 hexane/ethyl acetate elution to remove the alcohol and acid residues present in the product.

20.8 g of a pale yellow solid were finally obtained (this is a pure isolated product yield of 52% based on the starting acid). The structure was confirmed by mass spectrometry and by proton magnetic resonance ($^1$H NMR). Purity was greater than 95%.

Physical characteristics

---
Melting point: 30° C.
UV (CHCl$_3$ solvent): ε 327 nm = 18850 l mol$^{-1}$ cm$^{-1}$
ε 287 nm = 30265 l mol$^{-1}$ cm$^{-1}$
---

EXAMPLE 3

Preparation of the product (Ic): esterification product of 1,3-di(4-benzoyl-3-hydroxyphenoxy)2-propanol with the diacid of formula (V):

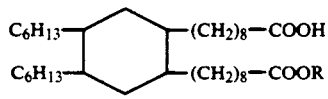

(V)

The following were charged into a 500 cc three-necked round bottom flask fitted with a central stirrer, a thermometer and a Dean-Stark trap, supporting a condenser under nitrogen atmosphere:

25.0 g (0.052 mol) of alcohol of formula (II)

13.9 g (0.024 mol) of the diacid (V)

1.0 g of para-toluenesulfonic acid, 250 cc of toluene.

The reaction mixture was heated to the reflux temperature of toluene for 24 hours. After returning to room temperature, the reaction mixture was washed three times with 150 cc of water. The organic phase was then dried over sodium sulfate and the toluene was evaporated off at reduced pressure. The 28.7 g of crude product that was recovered was chromatographed on a column of silica gel with 2/1 hexane/ethyl acetate elution to remove the alcohol and acid residues present in the product.

23.5 g of a viscous pale yellow liquid were finally obtained (this is a pure isolated product yield of 64% based on the starting acid). The structure was confirmed by proton magnetic resonance ($^1$H NMR). Purity was about 90%.

---
UV (CHCL$_3$ solvent): ε 327 nm = 36310 l mol$^{-1}$ cm$^{-1}$
ε 287 nm = 58320 l mol$^{-1}$ cm$^{-1}$
---

EXAMPLE 4

Products (Ia) and (Ib) were evaluated alone and in combination with 2-hydroxy-4-octyloxybenzophenone (RHODIALUX P ®) marketed by Rhodia SpA) as UV stabilizers in accelerated UV aging of polypropylene (PP).

Preparation of the compositions

Mixtures of the composition by weight shown below were prepared in a slow mixer:

Polypropylene: 100 g

Calcium stearate: 0.1 g

IRGANOX 1076 ® antioxidant : 0.05 g

Products I(a), I(b) and RHODIOLUX P ®: according to Table 1

IRGANOX 1076 ® is the trademark of the Ciba-Geigy Corporation for octadecyl 3-(4-hydroxy-3,5-di-tert-butylphenl)propionate. The polypropylene was APPRYL 3030 AP ®.

Pressing

The mixtures were then pressed twice in a Carver press at 190° C.: the first time for 5 min, 3 min of which are under a pressure of 30 MPa (300 bars), and the second time for 5 min, 3 min of which are under a pressure of 35 MPa (350 bars). Films of 50 μm were obtained. Samples of 12×30 mm were cut from each sheet.

Aging

These samples were placed in a MPC/SEPAP 12/24 chamber heated to 60° C. and equipped with 4 "medium pressure" mercury vapor lamps of the Mazda MA 400 W type. The degradation of the polypropylene films was followed in the infrared by the appearance of the carbonyl band at 1720 cm.$^{-1}$. The results are presented in Table 1.

The lifetimes in hours correspond to the times taken to reach a given absorbance. In this case, log(I-O/I)=0.3.

TABLE 1

| Compositions | UV absorber (in g per 100 g of PP) | | Lifetime |
|---|---|---|---|
| 4.1 | RHODIALUX P ® | 0.35 | 375 |
| 4.2 | Product Ia | 0.35 | 238 |
| 4.3 | Product Ib | 0.35 | 257 |
| 4.4 | RHODIALUX P ® | 0.18 | 336 |
|     | Product Ia | 0.17 | |
| 4.5 | RHODIALUX P ® | 0.18 | 386 |
|     | Product Ib | 0.17 | |
| 4.6 | RHODIALUX P ® | 0.25 | 330 |
|     | Product Ia | 0.10 | |
| 4.7 | RHODIALUX P ® | 0.25 | 354 |
|     | Product Ib | 0.10 | |
| 4.8 | RHODIALUX P ® | 0.30 | 400 |
|     | Product Ia | 0.05 | |
| 4.9 | RHODIALUX P ® | 0.30 | 408 |
|     | Product Ib | 0.05 | |

EXAMPLE 5

Products (Ia) and (c) were evaluated in combinations with RHODIALUX P ® and TINUVIN 770 ® (bis(2,2,6,6-tetramethyl-4-piperidrnyl) decanoate by Ciba-Geigy) in accelerated UV aging of polupropylene.

Preparation of the compositions

Mixtures of the composition by weight shown below were prepared in a slow mixer:
APPRYL 3030 AP ®PP: 100 g
Calcium stearate: 0.1 g
IRGANOX 1076® antioxidant: 0.05 g
TINUVIN 770® HALS P 0.15 g
Products (Ia) (Ic) and RHODIALUX P ®: according to Table 2.

Pressing of the films and aging of the samples were performed in the same way as in Example 4. The results are presented in Table 2.

The lifetimes in hours correspond to the time taken to reach a given absorbance. In this case log(Io/I)=0.3.

TABLE 2

| Compositions | UV absorber (in g per 100 g of PP) | | Lifetime |
|---|---|---|---|
| 5.1 | Control without UV absorber | | 241 |
| 5.2 | RHODIALUX P ® | 0.35 | 366 |
| 5.3 | Product Ia | 0.35 | 283 |
| 5.4 | Product Ic | 0.35 | 331 |
| 5.5 | RHODIALUX P ® | 0.30 | 455 |
|     | Product Ia | 0.05 | |
| 5.6 | RHODIALUX P ® | 0.30 | 402 |
|     | Product Ic | 0.05 | |
| 5.7 | RHODIALUX P ® | 0.25 | 395 |
|     | Product Ia | 0.10 | |
| 5.8 | RHODIALUX P ® | 0.25 | 427 |
|     | Product Ic | 0.10 | |

We claim:

1. An organic polymer composition stabilized against UV degradation with an effective amount between about 0.005 and 5 weight percent based on the weight of said organic polymer, of at least one benzophenone compound having the general formula (I)

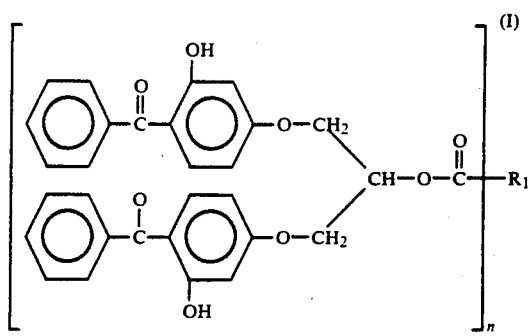

wherein n is 2, and
R$_1$ is a radical having 6 to 40 carbon atoms and represents a linear or branched alkylene radical, an ortho-phenylene, meta-phenylene or para-phenylene radical having 0-2 linear or branched alkyl substituents having from 1 to 6 carbon atoms, an ortho-dialkylene cyclohexane radical in which the alkylene radicals, which can be linear or branches, identical or different, have from 1 to about 12 carbon atoms; an orthocyclohexylene, meta-cyclohexylene or para-cyclohexylene radical; or a cyclohexylene or ortho-dialkylene cyclohexane radical as described above, having 1 or 2 linear or branched-chain alkyl substituents having from 1 to 6 carbon atoms.

2. A composition according to claim 1 wherein the organic polymer is selected from the class consisting of polyolefins, polystyrenes, norbornene polymers, polyalkadienes, polyurethanes, polyether-sulfones, polyether-ketones, acrylic polymers, halogenated polymers and copolymers and mixtures thereof.

3. An organic polymer composition according to claim 1 wherein R$_1$ is a linear or branched alkylene radical having 12 to 40 carbon atoms, a cyclohexylene radical or a cyclohexylene radical having 1 or 2 linear or branched alkyl substituents having 1 to 6 carbon atoms.

4. An organic polymer composition according to claim 3 wherein the organic polymer is selected from the group consisting of polyolefins, polystyrenes, norbonene polymers, polyalkadienes, polyurethanes, polyether-sulfones, polyether-ketones, acrylic polymers, halogenated polymers and copolymers and mixtures thereof.

5. An organic polymer composition according to claim 1 wherein the benzophenone compound is bis[1,3-di-4-benzoyl-3-hydroxyphenoxy)-2-propyl] (4,5-dihexylcyclohexane)-1,2-octamethylene carboxylate.

6. An organic polymer composition according to claim 5 wherein the organic polymer is polypropylene.

7. An organic polymer composition stabilized against UV degradation with an effective amount between about 0.005 and 5 weight percent based on the weight of said organic polymer, of at least one benzophenone compound having the general formula (I)

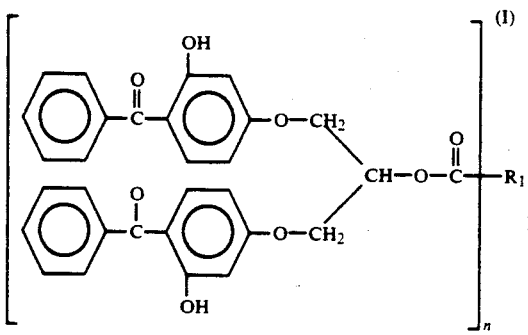

wherein n is 1 to 2, and $R_1$ when n is 1, is a radical having 6 to 40 carbon atoms and represents: a linear or branched alkyl radical; a phenyl radical or a phenyl radical having 1 or 2 linear or branched-chain alkyl substituents having 1 to 6 carbon atoms or a hydroxyl radical and $R_1$, when n is 2, is a radical having 6 to 40 carbon atoms and represents a linear or branched alkylene radical, an ortho-phenylene, meta-phenylene or para-phenylene radical having 0-2 linear or branched alkyl substituents having from 1 to 6 carbon atoms, an ortho-dialkylene cyclohexane radical in which the alkylene radicals, which can be linear or branched, identical or different, have from 1 to about 12 carbon atoms; an ortho-cyclohexylene, meta-cyclohexylene or para-cyclohexylene radical; or a cyclohexylene or ortho-dialkylene cyclohexane radical as described above, having 1 or 2 linear or branched-chain alkyl substituents having from 1 to 6 carbon atoms and further including an effective amount of at least one benzophenone compound of the general formula IV.

8. An organic polymer composition according to claim 7 wherein n is 1 and $R_1$ is a linear or branched alkyl radical having 12 to 40 carbon atoms.

9. An organic polymer composition according to claim 8 wherein the organic polymer is selected from the group consisting of polyolefins, polystyrenes, norbornene polymers, polyalkadienes, polyurethanes, polyether-sulfones, polyether-ketones, acrylic polymers, halogenated polymers and copolymers and mixtures thereof.

10. An organic polymer composition according to claim 9 wherein the benzophenone compound is selected from the group consisting of 1,3-di(4-benzoyl-3-hydroxyphenoxy)-2-propyl decanoate); 1,3-di(4-benzoyl-3-hydroxyphenoxy)-2-propyl dodecanoate; 1,3-di(4-benzoyl-3-hydroxyphenoxy)-2-propyl hexadecanoate; 1,3-di(4-benzoyl-3-hydroxyphenoxy)-2-propyl octadecanoate; and 1,3-di(4-benzoyl-3-hydroxyphenoxy)-2-propyl docosanoate.

11. An organic polymer composition according to claim 10 wherein the organic polymer is polypropylene.

12. An organic polymer composition according to claim 7 wherein n is 2 and $R_1$ is a linear or branched-chain alkylene radical having 12 to 40 carbon atoms, a cyclohexylene radical or a cyclohexylene radical having 1 or 2 linear or branched alkyl substituents having 1 to 6 carbon atoms.

13. An organic polymer composition according to claim 12 wherein the organic polymer is selected from the group consisting of polyolefins, polystyrenes, norbornene polymers, polyalkadienes, polyurethanes, polyether-sulfones, polyether-ketones, acrylic polymers, halogenated polymers and copolymers and mixtures thereof.

14. An organic polymer composition according to claim 13 wherein the benzophenone compound is bis[1,3-di-4-benzoyl-3-hydroxyphenoxy)-2-propyl] (4,5-dihexylcyclohexane)-1,2-octamethylene carboxylate.

15. An organic polymer composition according to claim 14 wherein the organic polymer is polypropylene.

16. A benzophenone compound of the general formula (I)

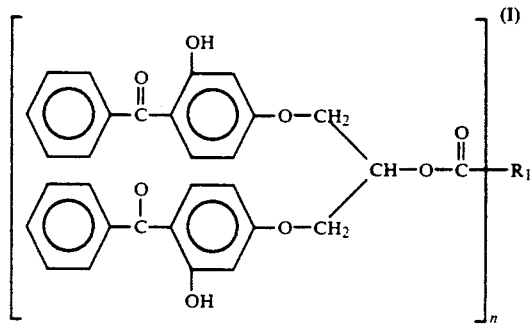

wherein $R_1$ is a radical having 6 to 40 carbon atoms and represents a linear or branched alkylene radical, an ortho-phenylene, meta-phenylene, or para-phenylene radical containing 0 to 2 linear or branched alkyl substituents having 1 to 6 carbon atoms; an ortho-dialkylene cyclohexane radical in which the alkylene radicals have about 1 to 12 carbon atoms, an ortho-cyclohexylene, meta-cyclohexylene or para-cyclohexylene radical; or a cyclohexylene or ortho-dialkylene cyclohexane radical containing 1 or 2 linear or branched alkyl substituents having 1 to 6 carbon atoms.

17. A benzophenone compound according to claim 16 wherein $R_1$ is an ortho-dialkylene cyclohexane radical containing 2 linear or branched alkyl substituents having 1 to 6 carbon atoms.

18. A benzophenone compound according to claim 17 wherein the alkylene radicals are octamethylene radicals and the alkyl radicals are n-hexyl radicals.

* * * * *

UNITED STATES PATENT AND TRADEMARK OFFICE
CERTIFICATE OF CORRECTION

PATENT NO.   : 5,281,645
DATED        : January 25, 1994
INVENTOR(S)  : Philippe Chicart et al.

It is certified that error appears in the above-indentified patent and that said Letters Patent is hereby corrected as shown below:

Claim 1, column 8, line 24, change "branches" to --branched--.

Claim 4, column 8, lines 50-51, change "norbonene" to --norbornene--.

Claim 7, column 9, line 17, change "$R_1$when" to --$R_1$, when--.

Signed and Sealed this

Twentieth Day of September, 1994

Attest:

BRUCE LEHMAN

*Attesting Officer*      *Commissioner of Patents and Trademarks*